(12) United States Patent
Wells et al.

(10) Patent No.: US 7,235,258 B1
(45) Date of Patent: Jun. 26, 2007

(54) SUSTAINED-RELEASE FORMULATIONS FOR TREATING CNS-MEDIATED DISORDERS

(75) Inventors: David S. Wells, Sandy, UT (US); Lian G. Rajewski, Lawrence, KS (US); Thomas B. Marriott, Sandy, UT (US); James D. Pipkin, Lawrence, KS (US); John L. Haslam, Lawrence, KS (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 09/691,237

(22) Filed: Oct. 19, 2000

Related U.S. Application Data (60) Provisional application No. 60/160,210, filed on Oct. 19, 1999.

(51) Int. Cl.
*A61K 9/22* (2006.01)
*A61K 9/20* (2006.01)

(52) U.S. Cl. ............... 424/468; 424/464; 424/472; 424/476; 424/480

(58) Field of Classification Search ............... 424/472, 424/471, 473, 479, 480, 482, 468, 469, 481; 514/629, 923
See application file for complete search history.

(56) References Cited

U.S. PATENT DOCUMENTS

| | | | |
|---|---|---|---|
| 4,428,858 A | 1/1984 | Cognard et al. | 252/289.1 |
| 4,571,333 A * | 2/1986 | Hsiao et al. | 424/465 |
| 4,880,830 A | 11/1989 | Rhodes | 424/470 |
| 4,996,061 A | 2/1991 | Webb et al. | 424/475 |
| 5,256,440 A | 10/1993 | Appel et al. | 427/8 |
| 5,366,738 A * | 11/1994 | Rork et al. | 424/473 |
| 5,399,359 A | 3/1995 | Baichwal | 424/464 |
| 5,415,871 A * | 5/1995 | Pankhania et al. | 424/468 |
| 5,506,268 A | 4/1996 | Balandrin et al. | 514/629 |
| 5,582,838 A * | 12/1996 | Rork et al. | 424/472 |
| 5,672,359 A | 9/1997 | Digenis et al. | 424/463 |
| 5,674,895 A | 10/1997 | Guittard et al. | 514/534 |
| 6,589,994 B1 * | 7/2003 | Artman et al. | 514/629 |

FOREIGN PATENT DOCUMENTS

| | | |
|---|---|---|
| WO | 94/28888 | 12/1994 |
| WO | 98/08498 | 3/1998 |
| WO | WO 98/08498 | 3/1998 |
| WO | WO 99/44623 | * 10/1999 |

OTHER PUBLICATIONS

Chemical Abstract, vol. 83, No. 14, Oct. 6, 1975, T.A. Grosovyi et al. "Development of an Optimum Intestine Soluble Film-Forming Composition from Cellulose Acetate Phthalate for Tablet Coating in a Fluidized Bed".

Pharmaceutical Journal, No. 2, 1975, UDC 515.453.6, T.A. Groshovy, et al. Development of Optimal Intestine-Soluble Film-Forming Acetylphthalylcellulose-Based Compositions for Fluidized-Bed Coating of Tablets.

* cited by examiner

*Primary Examiner*—Lakshmi S. Channavajjala
(74) *Attorney, Agent, or Firm*—TraskBritt, PC (57) ABSTRACT

Sustained-release compositions for delivering therapeutic concentrations of isovaleramide, isovaleric acid, and certain structurally related compounds are provided for the treatment for a variety of pathological conditions, including epilepsy and spasticity, which are ameliorated by effecting a modulation of CNS activity. The ability of the compositions to sustain relatively constant levels of the drug at a therapeutic dose in the serum for extended periods of time enables a once or twice daily administration schedule.

8 Claims, 6 Drawing Sheets

Figure 1a. The Structures of Isovaleramide and Related Compounds.

Figure 1b: Structures of compounds structurally related to isovaleramide

Figure 4. NPS 1776 Release From Coated MPC Formulations

Figure 5. NPS 1776 Release From Coated MPC Formulations

SUSTAINED-RELEASE FORMULATIONS FOR TREATING CNS-MEDIATED DISORDERS

This application claims the benefit of U.S. Provisional application No. 60/160,210 filed on Oct. 19, 1999.

FIELD OF THE INVENTION

This invention relates to the effective treatment of pathological conditions, such as convulsions, bipolar affective disorder, migraine, anxiety and spasticity, the symptoms of which are alleviated by a modulation of activity in the central nervous system (CNS), without producing undesirable excessive sedation or muscle weakness. More particularly, the invention relates to the preparation and use of sustained-release formulations of isovaleramide, isovaleric acid, and related compounds for treatment of patients suffering from such conditions.

BACKGROUND OF THE INVENTION

A number of pathological conditions are characterized by a profound aberration in the normal function of the CNS. Such conditions include, for example, epilepsy, stroke, bipolar affective disorder, migraine, anxiety, spasticity, spinal cord injury, chronic neurodegenerative disorder and diseases such as Parkinson's disease, Huntington's disease, and Alzheimer's disease. At the clinical level, these conditions usually respond only to pharmacologic intervention with compounds or substances that possess significant activity at the level of the CNS.

Isovaleramide, isovaleric acid and related compounds have been described for treating abnormalities of the CNS, such as epilepsy. These compounds provide a therapeutic approach by effecting a modulation of CNS activity without producing excessive sedation, muscle weakness, fatigue, teratogenicity or hepatotoxicity.

It has been discovered herein that orally administered isovaleramide has a short half-life in humans. In the absence of an approach to reduce the rate of uptake of drug following administration, the short half-life requires that isovaleramide be administered frequently to sustain a therapeutic concentration of the drug without adverse effects. Frequent dosing schedules increase costs and raise concerns of patient compliance. Thus, it would be desirable to have a sustained-release formulation of isovaleramide, isovaleric acid and related compounds that can be administered on a once or twice per day schedule for the effective treatment of epilepsy and other pathological conditions of the CNS.

SUMMARY OF THE INVENTION

Accordingly, it is an object of the present invention to provide a composition comprising a sustained-release drug formulation for sustained delivery of isovaleramide, isovaleric acid, and related compounds for the treatment of various pathologies by effecting a modulation of CNS activity without producing excessive sedation, muscle weakness, fatigue, teratogenicity or hepatotoxicity. Such a composition is useful for treatment of convulsions, spasticity, affective mood disorder, neuropathic pain syndrome, migraine and other headache pathologies, restlessness syndrome, movement disorder, substance abuse/craving, cerebral trauma and anxiety-related disorders such as restlessness, nervousness, inability to concentrate, over-aggressiveness, irritability, and insomnia as well as symptoms of smoking cessation, treatment of alcoholism and other substance abuse, premenstrual syndrome, menstrual discomfort, and hyperexcitability in children.

In accomplishing these and other objectives, there has been provided, according to one aspect of the present invention, a pharmaceutical composition comprising a sustained-release formulation of isovaleric acid, isovaleramide and related compounds. Upon oral administration, the sustained-release formulation releases the active compound over a period of at least 8 to 12 hours (h). With such a formulation, only two administrations of the drug need to be given each day.

In accordance with another embodiment of the present invention, the sustained-release composition comprises a matrix, wherein the matrix comprises a gelling agent that dissolves slowly and/or resists hydration. In one embodiment, the gelling agent is xanthan gum. In another embodiment, the active compound is dispersed in the matrix.

In accordance with another embodiment of the present invention, the sustained-release composition comprises a film-coating that retards access of liquids to the active compound and/or retards release of the active compound through the film-coating.

In accordance with yet another embodiment of the present invention, the sustained-release composition comprises one or more excipients that assist in formulation.

In accordance with still another embodiment of the present invention, the sustained-release composition comprises a core wherein the core comprises a compressed mixture of the therapeutically effective unit dose of the active compound and a matrix material, and a film-coating around the core. In another embodiment, the matrix material dissolves slowly and/or resists hydration, while in another embodiment, the matrix material is xanthan gum.

In accordance with another embodiment, the composition further comprises one or more excipients to assist in formulation.

In accordance with yet another embodiment, the film coating comprises a polymeric coating material. In a further embodiment, the polymeric material comprises a mixture of ethyl cellulose and hydroxypropyl methylcellulose, and in another embodiment, further comprises a plasticizer.

In accordance with still yet another embodiment, the sustained-release composition is in the form of a tablet, capsule, or multiparticulate composition.

In accordance with another aspect of the present invention, a process is provided for producing the sustained-release formulations described above.

In accordance with yet another aspect of the present invention, methods are provided for treating CNS mediated pathologies and conditions by administering the sustained-release compositions described above.

Other objects, features, and advantages of the present invention will become apparent from the following detailed description. It should be understood, however, that the detailed description and the specific examples, while indicating preferred embodiments of the present invention, are given by way of illustration only, since various changes and modifications within the spirit and scope of the invention will become apparent to those skilled in the art from this detailed description.

DETAILED DESCRIPTION OF THE PREFERRED EMBODIMENTS

1. Overview

Isovaleric acid and its pharmaceutically acceptable salts, amides such as isovaleramide, alcohol esters and structurally related compounds effect a modulation of CNS activity and are useful for treating epilepsy and a variety of other CNS disorders. As described below (Example 1), orally administered isovaleramide is readily absorbed from the gastrointestinal tract and rapidly eliminated in human subjects, exhibiting a half-life of about 2.5 hours for doses ranging from 100 to 1600 mg. These characteristics are inconvenient for using isovaleramide for oral treatment of CNS disorders because frequent dosing is required to maintain a therapeutic drug level, which could create problems with patient compliance and costs.

In response to this need, the present invention provides sustained-release compositions of isovaleramide and related compounds. The formulations disclosed herein are designed to deliver a specific amount of drug over a specific course of time to achieve a therapeutic plasma drug concentration, while minimizing peak to trough differences that occur in vivo. This is achieved despite the fact that the drug is very water soluble.

"Sustained Release" as used herein, means the release of an active compound whereby the level of active compound available to the host is maintained at some level over a period of time. This is distinguished from "controlled release" which typically is broadly defined to include instantaneous release, delayed release and sustained release concepts. "Instantaneous release" refers to immediate release to the biosystem of the host while "delayed release" means the active ingredient is not made available to the host until some time delay after administration. Although the compositions of the present invention are designed to achieve sustained release of the active compounds of the composition, instantaneous release and delayed release properties also can be designed into the instant compositions without departing from the spirit of the invention.

2. Preparation of Sustained-Release Formulations

Identification of Active Compounds

Active compounds for treating CNS disorders include isovaleric acid, a pharmaceutically acceptable salt of isovaleric acid, a pharmaceutically acceptable ester of isovaleric acid, a pharmaceutically acceptable amide of isovaleric acid, and related compounds as described in WO 98/08498A1 and U.S. Pat. No. 6,589,994. As described therein, isovaleric acid is available from extracts of the rhizomes and roots of *Valeriana* spp. (common name: valerian; family Valerianaceae) and ammonium isovalerate and isovaleramide are produced in ammoniated tinctures of the extracts.

Generally, esters of isovaleric acid are expected to be hydrolyzed in vivo by ubiquitous esterase enzymes, thereby releasing isovaleric acid and the constituent alcohol. In addition to isovaleramide, various N-substituted amides of isovaleric acid also are described in WO 98/08498A1 and U.S. Pat. No. 6.589,994.

Figure 1A:
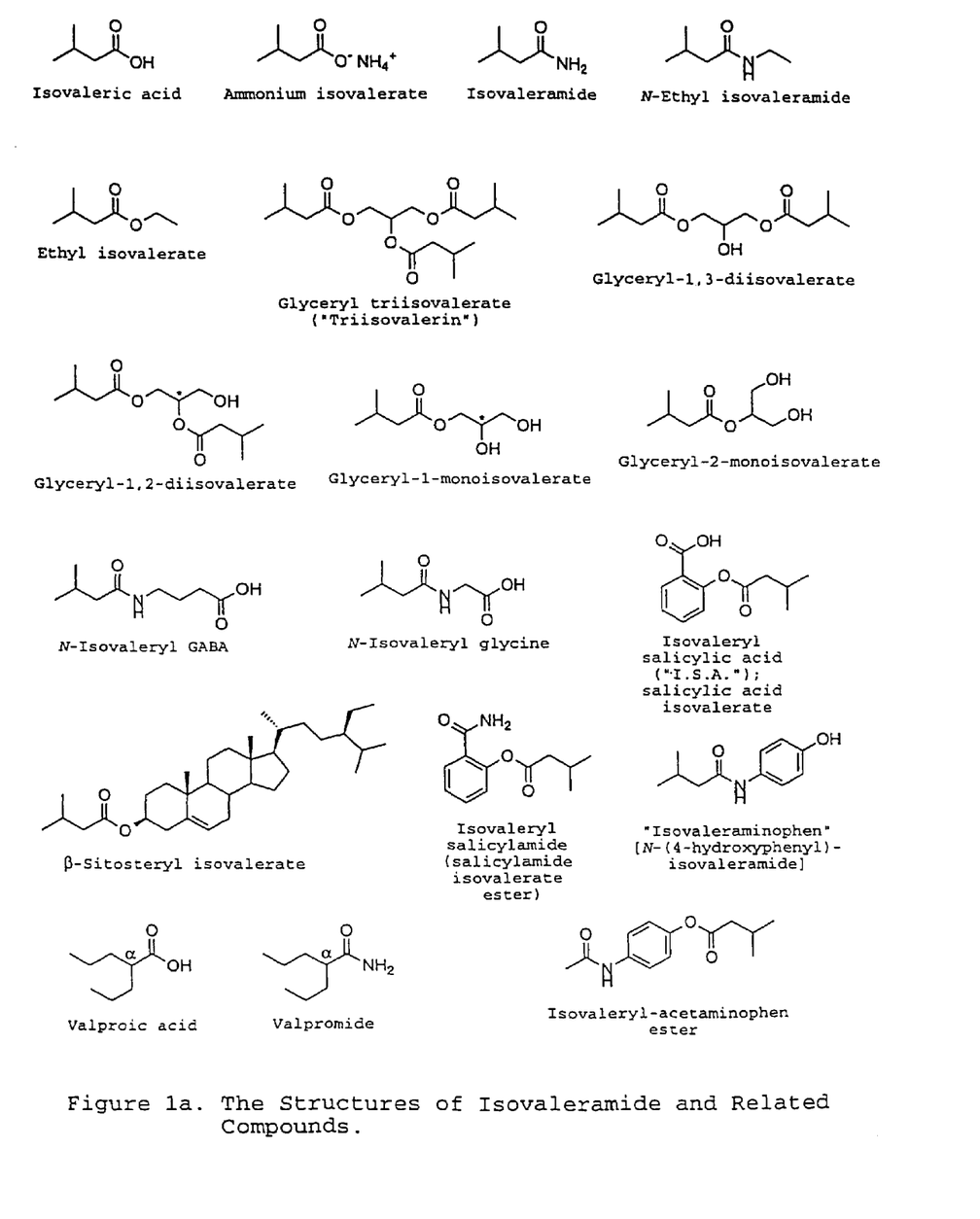
FIGS. 1a and 1b depict the structures of compounds, including isovaleramide, capable of inducing a modulation of the central nervous system.
Figure 1B:
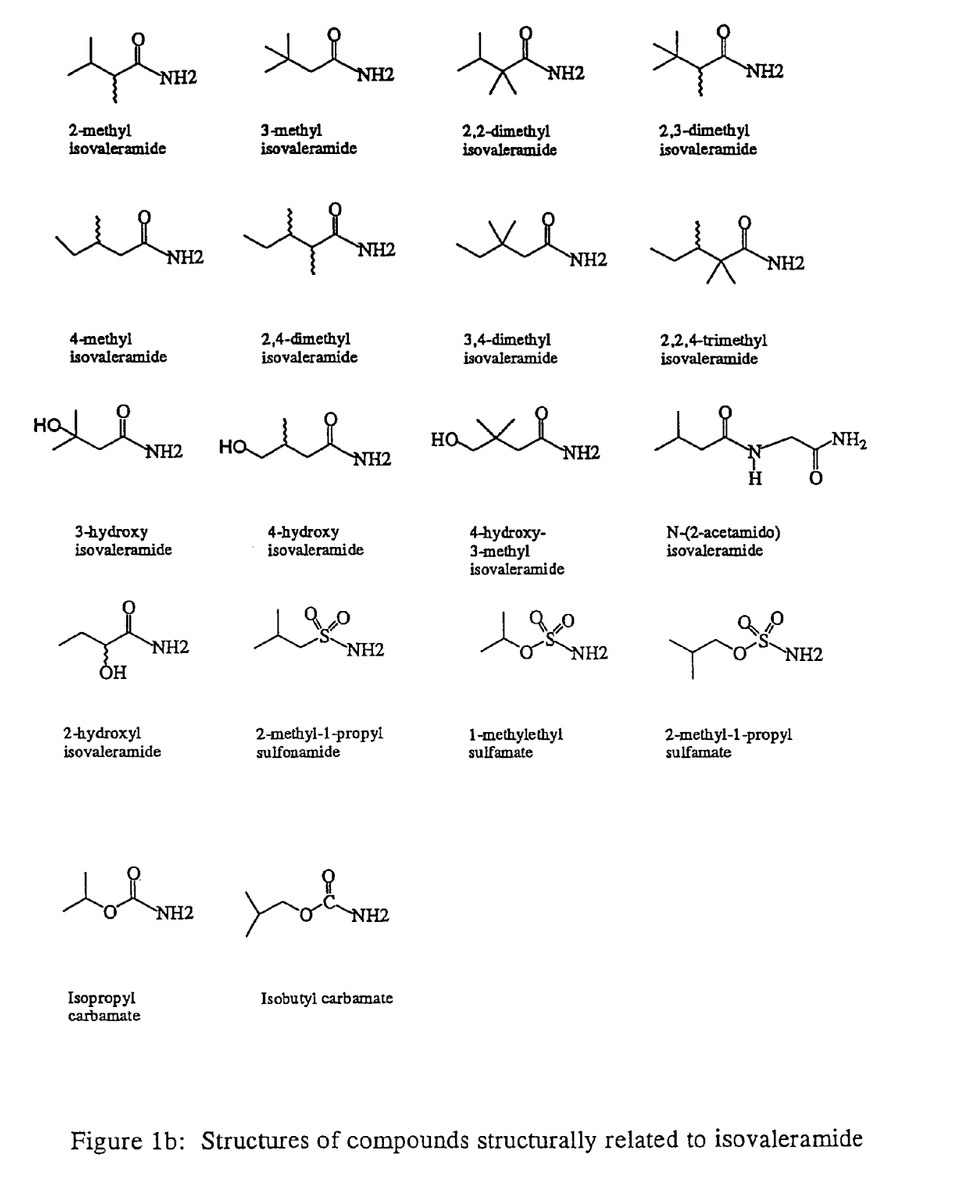
Figure 2:
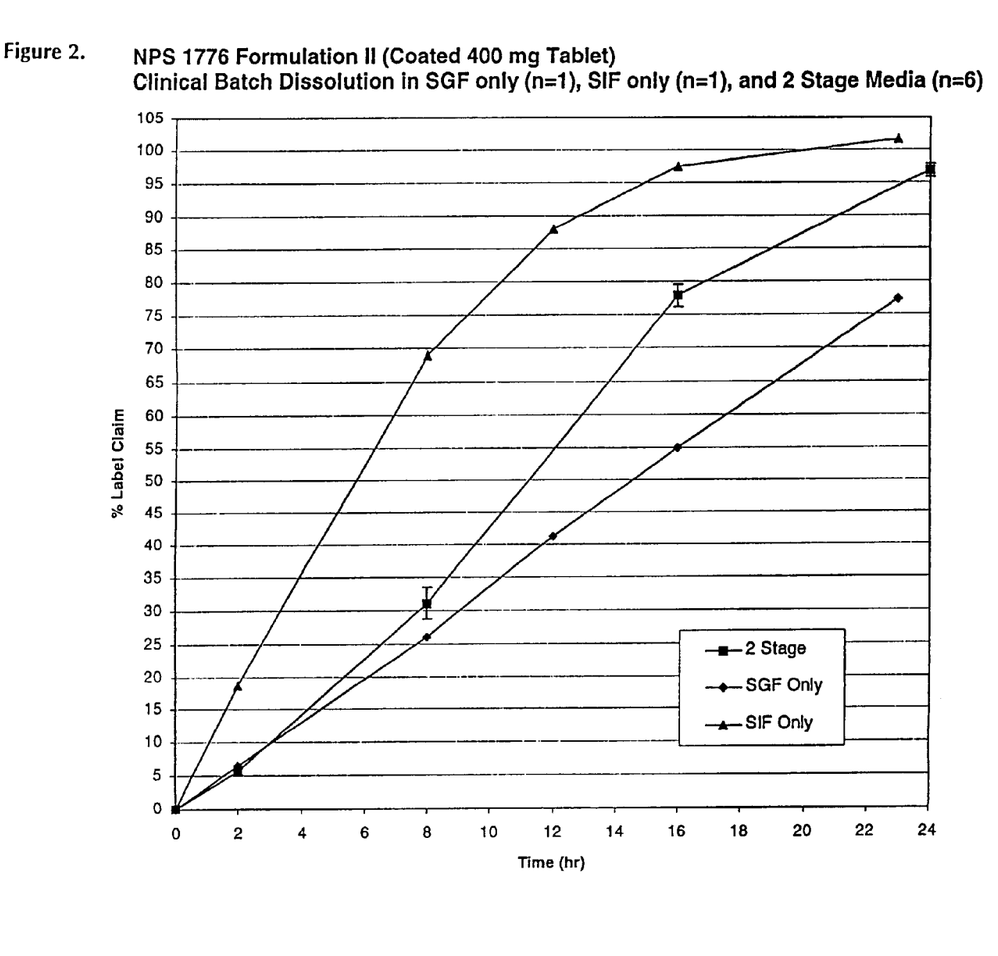
FIG. 2 portrays a 24-hour dissolution profile of film-coated sustained-release tablets containing 400 mg of isovaleramide (Formulation II, Example 2.1). Dissolution is performed in two-stage media essentially as described in Example 2.1 using simulated gastric fluid without enzymes (SGF) followed by simulated intestinal fluid without enzymes (SIF). Dissolution in SGF and SIF alone also is analyzed. Percent of drug released as determined by HPLC (% label claim) is plotted on the Y axis versus time (hours) on the X axis. At 16 hours, over 75% of the drug is released under the two-stage media analysis. Drug release efficiency is greater in SIF as compared to SGF as shown by the individual dissolution profiles.

Active compounds also include compounds structurally similar to isovaleramide and that share similar pharmacological activities. These compounds generally share the common structure:

Where
A=H, $CH_3$ or OH,
B=H, OH, or $CH_3$,
X=$CH_2$, $CHCH_3$, $C(CH_3)_2$, —O—, $CH(OH)$—, or —$CH_2O$—,
Y=—CO—, or —$SO_2$—, and
Z=H, $CH_2CO_2H$, or $CH_2CONH_2$ The structures of these compounds are shown in FIGS. 1a and 1b and include substituted isovaleramides such as 2-methylisovaleramide, 3-methylisovaleramide, 2,2-dimethylisovaleramide, 2,3-dimethylisovaleramide, 4-methylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, and 2,2-dimethyl-n-butyramide. For each of these compounds that contains one or more asymmetric centers, the present invention specifically includes each of the possible enantiomeric or diastereomeric forms of the compound.

N,N-Diethyl isovaleramide ("Valyl"), although purported to possess CNS depressant (sedative) activity, recently has been shown to possess CNS stimulant (convulsant) properties (U.S. Pat. No. 5,506,268 and PCT application WO 94/28,888). An amide of isovaleric acid with p-aminophenol also can be prepared using standard methods to provide a compound, "isovaleraminophen," which is related structurally to the drug acetaminophen (Tylenol®). In a manner analogous to that of the isovalerate esters, these substituted amides should be hydrolyzed in vivo (in this case, via hepatic amidase enzymes), releasing isovaleramide or isovaleric acid.

In addition to the amide compounds described above, the active compounds useful in the sustained-release formulations of the present invention, include the sulfonamide, sulfamate, and carbamate compounds of isovaleric acid that, by virtue of their structural similarity to isovaleramide, share similar pharmacological activities. Preferred sulfonamides and sulfamates include 2-methyl-1-propylsulfonamide, 1-methylethyl sulfamate, and 2-methyl-1-propyl sulfamate. Preferred carbamates include isobutylcarbamate $(CH_3)_2CHCH_2OCONH_2)$ and isopropylcarbamate $(CH_3)_2CHOCONH_2)$.

Preparation of Active Compounds

The compounds of the present invention may be prepared using synthetic methods that are well known in the art. For example, many of the carboxylic acid precursors of the amide compounds are commercially available (e.g., Aldrich Chemical Co., Milwaukee, Wis.) and can be converted into the corresponding amide by preparation of the acid chloride with thionyl chloride or oxalyl chloride, followed by reaction with ammonia or an amine. For compounds containing a hydroxyl group distal to the carboxyl group, the hydroxyl group first is protected using a suitable protecting group as described, for example, in Green, "Protective Groups in Organic Synthesis," Wiley Press (1981), prior to preparation of the acid chloride. 2-hydroxy and 3-hydroxy isovaleramide are metabolites of isovaleramide in vivo, and can be isolated in high yield from the urine of a patient being treated with isovaleramide.

For compounds where the starting acid is not commercially available, the required acid can be prepared by straightforward methods of organic synthesis known to the skilled chemist. For example, carboxylic acid esters may be deprotonated with a strong non-nucleophilic base, such as lithium diisopropylamide, followed by alkylation with methyl iodide or methyl trifluoromethanesulfonate. The alkylated ester is hydrolyzed and converted to the amide by the methods described above.

When the compounds contain one or more asymmetric centers, the individual enantiomers may be prepared from optically active starting materials, or separated by traditional methods of resolution, such as fractional crystallization of salts with chiral amines, or by preparation of amides with chiral amides, chromatographic separation, and hydrolysis of the amides. Alternatively, the amides can be prepared by well-known methods of asymmetric synthesis, such as alkylation of an ester or amide of the acid prepared using a chiral auxiliary. For example, see Evans et al., *Tetrahedron*, 44:5525 (1988), and Fadel et al., *Tetrahedron: Asymmetry*, -vol. 5:4, pp. 531-534, 1994.

The present invention thus contemplates a variety of pharmaceutical compositions containing the active compounds described above (including isovaleramide, isovaleric acid, and/or its pharmaceutically acceptable salts, substituted amides, alcohol esters, sulfonamide, sulfamate, and carbamate analogs) as active ingredients in a sustained-release formulation that is suitable for oral, IV, parenteral, transdermal, transmucosal, intranasal, buccal, or rectal administration. Although such compounds may be present as incidental by-products in certain pharmaceutical formulations which are outside the scope of the present invention, the common feature of the present formulations is that isovaleramide, isovaleric acid, and/or its pharmaceutically acceptable salts, substituted amides, alcohol esters, and sulfonate, sulfamate, and carbamate analogs, are present in a standardized amount. That is, the pharmaceutical formulations contain a predetermined, chemically-defined, and quantifiable amount of at least one of such compounds to enable the determination of the quantity of a particular composition required to achieve the dosage levels described herein.

Sustained-Release Compositions

The present invention provides sustained-release pharmaceutical compositions comprising the active compounds described above. The pharmaceutical compositions can contain a single active compound or a combination of two or more of the active compounds. Also, isovaleramide and/or related compounds can be used in combination with other pharmaceutically active ingredients.

A "unit" of drug herein refers to an individual item containing drug, such as a capsule or tablet. "Unit dose" denotes the amount of drug contained in a unit of the drug. The term "dose" or "dosage" refers to the amount of drug administered at a single point in time. For example, oral administration of two units (e.g., tablets) at a single point in time, each having a unit dose of 100 mg of drug, results in a drug dose of 200 mg. "Daily dose" means the amount of drug administered over a one day (24-hour) period.

The sustained-release composition of the present invention can comprise any unit dose of active compound, generally between about 100 to 1200 mg. Preferable unit doses of 300 mg and 600 mg can be administered in a variety of combinations to obtain doses of 300, 600, 900, 1200, 1500, 1800, 2100, and 2400 mg. Smaller unit doses can be produced for pediatric administration, generally from about 50 to 300 mg in amount. A daily dose of drug could range between about 100 to 4800 mg, but more typically, would range between about 300 to 2400 mg.

The approach to determine drug treatment parameters, such as the total daily dosage, unit dose and schedule of administration, is well known and depends on a number of factors, including, for example, mode of administration, safety, tolerability, effectiveness, bioavailability and pharmacokinetic properties of the composition. Drug compositions with sustained-release properties can initially be screened for resistance to dissolution in an in vitro simulated gastric and intestinal environment (Example 3). Promising sustained-release compositions are then tested in vivo for safety, tolerability, effectiveness, bioavailability and pharmacokinetic properties (Examples 1 and 3).

Sustained-release formulations are designed to achieve a stable serum concentration of the drug over a convenient period of time (e.g., 12 hours) even though the drug has a short half-life. A stable drug level is achieved by releasing drug into the system at a sustained rate that approximates its rate of clearance. The amount of drug in each dose of the formulation depends on several factors including, for example, the effective therapeutic serum concentration of the drug as well as the bioavailability and pharmacokinetic properties of the drug in the sustained-release formulation. For example, the amount of isovaleramide active compound represents about 40-70% by weight of a sustained-release tablet, with the remainder of the composition providing sustained-release characteristics and/or assisting in formulation. Methods for determining and evaluating these characteristics are well known in the art.

An extensive variety of sustained-release compositions and devices have been described for sustained and controlled release of pharmaceutical compositions. For example, see Baker, CONTROLLED RELEASE OF BIOLOGICALLY ACTIVE AGENTS 73 (Wiley-Interscience, 1987); Heller, "Biodegradable Polymers in Controlled Drug Delivery," in 1 CRC CRITICAL REVIEWS IN THERAPEUTIC DRUG CARRIER SYSTEMS 39–90 (1987); Di Colo, "Controlled Drug Release From Implantable Matrices Based On Hydrophobic Polymers," *Biomaterials* 13: 850–56 (1992); CONTROLLED RELEASE TECHNOLOGIES: METHODS, THEORY, AND APPLICATIONS, Agis F. Kydonieus, ed. (CRC Press Inc., 1985). Many of the previously described approaches for sustained-release formulations can be adapted for sustained release of the active compounds described herein. One skilled in the art can manipulate the individual formulations to achieve a desired release rate of drug release in both in vitro and in vivo testing formats following the principles of sustained drug delivery discussed above. In addition, a variety of pharmaceutically acceptable carrier materials are known in the art (see, e.g., "Remington's Pharmaceutical Sciences," 18th ed., Gennaro, ed., Mack Publishing Company, Easton, Pa., 1990; and "The Pharmacological Basis of Therapeutics," Goodman and Gilman, eds., 8th Edition, Pergamon Press, 1990) and these can be included in sustained release formulations of the present invention.

The sustained-release composition of the present invention can be provided in solid unit form. It may be formed into any desired solid drug unit, including, for example, capsules, tablets, multiparticulate compositions, caplets, gelcaps, lozenges, suppositories, pessaries or implants.

The inventive compositions can be administered orally using solid oral drug units such as, tablets, caplets, gelcaps, capsules, granules, multiparticulate compositions, or using a liquid-based drug unit. These compounds also can be added to foods and beverages for oral administration, particularly in the case of drug granules which can be sprinkled on food. In addition, the sustained-release compositions can be formulated in chewable form (e.g., chewing gum) to facilitate oral delivery and absorption, particularly in pediatric applications. The inventive compositions also can be administered by injection or other systemic routes, such as transdermal or transmucosal administration, for example, nasally, buccally, or rectally, via suppositories. Oral administration is more convenient and, hence, is preferred.

Following oral administration, the sustained-release composition slowly releases the pharmacologically active ingredient within the body as the formulation progresses along the gastro-intestinal tract. In this regard, the gastro-intestinal tract is considered to be the abdominal portion of the alimentary canal, i.e., the lower end of the esophagus, the stomach and the intestines.

A typical sustained-release formulation of the present invention comprises the active compound and a matrix, where the matrix comprises a gelling agent that swells upon contact with aqueous fluid. The drug entrapped within the gel is released from the formulation slowly, upon dissolution of the gel, and then is available for uptake into the body at a sustained rate. The active compound can be evenly dispersed within the matrix or can be present as pockets of drug in the matrix. For example, the drug can be formulated into small granules which are dispersed within the matrix. In addition, the granules of drug also can include a matrix, providing a primary and a secondary matrix, as described in U.S. Pat. No. 4,880,830.

The gelling agent and film forming/gelling polymers are preferably a polymeric material, which can include, for example, any pharmaceutically acceptable water soluble or water insoluble slow releasing polymer such as xanthan gum, gelatin, cellulose ethers, gum Arabic, locust bean gum, guar gum, carboxyvinyl polymer, agar, acacia gum, tragacanth, veegum, sodium alginate or alginic acid, polyvinylpyrrolidone, polyvinyl alcohol, methyl cellulose (MC), carboxymethyl cellulose (CMC), hydroxypropyl methylcellulose, hydroxypropyl methyl cellulose (HPMC), hydroxypropyl cellulose (HPC), hydroxyethyl cellulose (HEC), ethylcellulose (EC), acrylic resins or mixtures of the above (e.g., U.S. Pat. No. 5,415,871). A particularly preferred polymer is xanthan gum.

The gelling agent of the matrix also can be a heterodisperse gum comprising a heteropolysaccharide component and a homopolysaccharide component which produces a fast-forming and rigid gel, as described, for example, in U.S. Pat. No. 5,399,359. The matrix also can include a crosslinking agent such as a monovalent or multivalent metal cations to add rigidity and decrease dissolution of the matrix, further slowing release of drug (id.). The amount of cross-linking agent to be added can be determined using methods routine to the ordinary skilled artisan.

The choice of gelling agent depends upon the active compound and the overall configuration of the sustained-release composition, although use within a range of 10 to 70 parts per 100 parts by weight of the active compound is generally preferred. In the case of an oral sustained release formulation, the amount of xanthan gum generally between 5% to 20% of the weight of the composition is preferred, an amount between 5 to 10% is more preferred and an amount of about 6% is most preferred.

Although in some situations, the active compound and matrix can together represent virtually a complete sustained-release formulation, in general, additional components that are necessary to further retard release of active compound or to assist in formulation (i.e., excipients) will be required. For example, in tablets and multiparticulate composition formulations containing 400 mg isovaleramide, the amount of gelling agent and drug is preferably about 30 to 70% of the formulation, more preferably about 40–60% of the formulation and most preferably about 50% of the formulation. In tablets with unit drug doses of 600 mg, the amount of gelling agent and drug is preferably about 50–90% of the formulation, more preferably about 65–75% of the formulation and, most preferably, about 72% of the formulation.

In multiparticulate composition formulations with unit drug doses of 600 mg, the amount of gelling agent and drug is preferably about 40–85% of the formulation, more preferably about 50–70% of the formulation and, most preferably, about 60% of the formulation.

The matrix of the sustained-release composition also can include one or more pharmaceutically acceptable excipients recognized by those skilled in the art, i.e., formulation excipients. Such excipients include, for example, binders: polyvinylpyrrolidone, gelatin, starch paste, microcrystalline cellulose (such as AVICEL PH 101®, available from FMC Pharmaceutical Division, Philadelphia, Pa.); diluents (or fillers): starch, pregelatinized cornstarch (such as STARCH 1500®, available from Colorcon, West Point,PA), sucrose, dextrose, lactose, fructose, xylitol, sorbitol, sodium chloride, dextrins, calcium phosphate, calcium sulphate; and lubricants: stearic acid, magnesium stearate, calcium stearate, Precirol (mixture of mono-, di- and triesters of palmitic and stearic acid with glycerol) and flow aids, for example, talc or colloidal silicon dioxide. Pregelatinized cornstarch, microcrystalline cellulose, and a mixture of lactose and magnesium stearate are preferred as a formulation excipient.

If necessary, such formulation excipients can be present in large quantities, particularly where the composition comprises a small amount of pharmacologically active ingredient. The relative amounts of excipient to drug and gelling agent (and/or other matrix components) or excipient to gelling agent depend on a number of factors. In general, with a unit drug dose of about 400 mg, the amount of excipient relative to gelling agent (and/or other matrix components) and drug in tablet formulations is preferably 30 to 60% by weight of the composition, more preferably about 30 to 50% by weight of the composition, and most preferably about 39%, by weight of the composition. With unit drug doses of 600 mg, the amount of excipient relative to gelling agent (and/or other matrix components) and drug is preferably about 10 to 30% by weight of the composition, more preferably about 15 to 20% by weight of the composition, and most preferably about 16% by weight of the composition. Thus, a preferred range of excipient is about 16–39% by weight of the composition.

The matrix of the sustained-release composition of the present invention can further include a hydrophobic material which slows hydration of the gelling agent without disrupting the hydrophilic nature of the matrix, as described in U.S. Pat. No. 5,399,359. In certain preferred embodiments of the present invention, the hydrophobic material is included in the matrix in an amount from about 1 to about 20 percent by weight and replaces a corresponding amount of the formulation excipient. A solvent for the hydrophobic material may be an aqueous or organic solvent, or mixtures thereof.

The hydrophobic polymer can include, for example, a hydrophobic cellulosic material such as alkylcellulose or ethylcellulose, polymers or copolymers derived from acrylic or methacrylic acid esters, zein, waxes, shellac, hydrogenated vegetable oils, waxes and waxy substances such as carnauba wax, spermaceti wax, candellila wax, cocoa butter, cetosteryl alcohol, beeswax, ceresin, paraffin, myristyl alcohol, stearyl alcohol, cetylalcohol and stearic acid. Other pharmaceutically acceptable hydrophobic materials are known to those skilled in the art.

Examples of commercially available alkylcelluloses are AQUACOAT® (aqueous dispersion of ethylcellulose available from FMC Pharmaceutical Division, Philadelphia, Pa.) and SURELEASE® (aqueous dispersion of ethylcellulose available from Colorcon, West Point, Pa.). Examples of commercially available acrylic polymers suitable for use as the hydrophobic material include EUDRAGIT® RS and RL (copolymers of acrylic and methacrylic acid esters having a low content (e.g., 1:20 or 1:40) of quaternary ammonium compounds) (Röhm America Inc., Piscataway, N.J.).

The sustained-release composition of the present invention also can include a film-coating that surrounds the active compound or a combination of the active with matrix to retard access of liquids to the active compound and/or retard release of the active compound through the film-coating. The film-coating can provide characteristics of gastroresistance and enterosolubility by resisting rapid dissolution of the composition in the digestive tract. Such film-coating can comprise gels, waxes, fats, emulsifiers, combination of fats and emulsifiers, polymers, starch, and the like.

Film-coatings for sustain release compositions preferably comprises a polymeric coating material such as a hydrophobic polymer, e.g., ethylcellulose, which is applied together with a plasticizer. The rate of drug release is effected by adjusting the amount of film-coating applied, the plasticizer type, the amount of plasticizer added, and by including release modifying agents such as aqueous polymers to the coating formulation.

In a tablet composition of the present invention, the film-coating generally represents about 5–15% by weight of the sustained-release composition. Preferably, the core by weight represents about between 88–91% (or about 90%) of the composition with the remaining 9% to 12% (or about 10%) provided by the coating.

In a multiparticulate composition formulation of the present invention, the film-coating generally represents about 1–10% by weight of the sustained-release composition. Preferably, the core by weight represents about between 92–96% of the composition with the remaining 4% to 8% (or about 6%) provided by the coating.

Coating can be applied from a solution, suspension or as dry powder. A solution formulation can be in organic solvent or aqueous solvent. Aqueous solvent systems are preferred for general safety reasons. The active compound can be coated, either alone or combined with a matrix. The coating preferably is applied to the drug or drug and matrix combination as a solid core of material as is well known in the art.

Polymers useful for coating compositions of the present invention include a cellulosic derivative, for example, methylcellulose (METHOCEL® A: Dow Chemical Co., Midland, Mich.), HPMC with a molecular weight between 1,000 and 4,000,000 (METHOCEL® E: Dow Chemical; or PHARMACOAT®: Shin-Etsu Chemical Co., Tokyo, Japan), hydroxypropyl cellulose with a molecular weight between 2,000 and 2,000,000, ethyl cellulose, cellulose acetate, cellulose triacetate, cellulose acetate butyrate, cellulose acetate phthalate, cellulose acetate trimellitate (Eastman Kodak), carboxymethylethyl cellulose (DUODCEL®: Lehmann & Voss, Hamburg, Germany), HPMC phthalate, ethylcellulose, methylcellulose. Other polymers useful in a coating composition include acrylic polymers such as polymethacrylic acid-methacrylic acid copolymer (Type A 1:1 EUDRAGIT® L100; Röhm Pharma Gmbh, Weiterstadt, Germany; Type B 1:2 EUDRAGIT® S100; and Type C 1:1 EUDRAGIT® L100-55, aqueous dispersion 30% solids, EUDRAGIT® L30D), poly(meth)acryl ester: poly(ethyl acrylate, methyl methacrylate 2:1), EUDRAGIT® NE30D aqueous dispersion 30% solids, polyaminomethacrylate EUDRAGIT® E100, poly(trimethylammonioethyl methacrylate chloride) ammoniomethacrylate copolymer, EUDRAGIT® RL30D and EUDRAGIT® RS30D, as well as carboxyvinyl polymers, polyvinylalcohols, glucans scleroglucans, mannans, and xanthans.

Aqueous polymeric dispersions useful for coating the present invention include EUDRAGIT® L30D and RS/RL30D, and NE30D, SURELEASE® (Colorcon, Orpington Kent, United Kingdom) brand ethyl cellulose, EC brand N-10F ethyl cellulose, AQUATERIC® (FMC, Philadelphia, Pa.) brand cellulose acetate phthalate, COATERIC® (Colorcon Inc., West Point, Pa.) brand Poly(vinyl acetate phthalate), and AQUACOAT®-brand hydroxypropyl methylcellulose acetate succinate. Most of these dispersions are latex, pseudolatex powder, or micronized powder mediums.

A plasticizing agent preferably is included in the coating to improve the elasticity and the stability of the polymer film and to prevent changes in the polymer permeability over prolonged storage. Suitable conventional plasticizing agents include, for example, diethyl phthalate, glycerol triacetate, acetylated monoglycerides, acetyltributylcitrate, acetyltriethyl citrate, castor oil, citric acid esters, dibutyl phthalate, dibutyl sebacate, diethyloxalate, diethyl malate, diethylfumarate, diethylphthalate, diethylsuccinate, diethylmalonate, diethyltartrate, dimethylphthalate, glycerin, glycerol, glyceryl triacetate, glyceryltributyrate, mineral oil and lanolin alcohols, petrolatum and lanolin alcohols, phthalic acid esters, polyethylene glycols, propylene glycol, rape oil, sesame oil, triacetin, tributyl citrate, triethyl citrate, and triethyl acetyl citrate, or a mixture of any two or more of the foregoing. Plasticizers which can be used for aqueous coatings include, for example, propylene glycol, polyethylene glycol (PEG 400), triacetin, polysorbate 80, triethyl citrate, diethyl d-tartrate.

A coating solution comprising a mixture of HPMC and aqueous ethylcellulose (e.g., AQUACOAT® brand) as the polymer and dibutyl sebacate as plasticizer is preferred for coating the tablet compositions of the present invention (AQUACOAT® ECD is an aqueous dispersion of ethylcellulose polymer comprising total solids (29–32%), ethylcellulose (24.5–29.5%) sodium lauryl sulfate (0.9–1.7%) cetyl alcohol (1.7–3.3%), hydrogen peroxide (<50 ppm), heavy metals (<10 ppm), total aerobic microbial count (<100 cfu/g), total yeast and mold count (<20 cfu/g) with a pH of 4.0–7.0 and a viscosity of 150 cps). Preferably, the plasticizer represents about 1–2% of the composition.

In addition to the polymers, the coating layer can include an excipient to assist in formulation of the coating solution. Such excipients may include a lubricant or a wetting agent. Suitable lubricants as excipients for the film coating include, for example, talc, calcium stearate, colloidal silicon dioxide, glycerin, magnesium stearate, mineral oil, polyethylene glycol, and zinc stearate, aluminum stearate or a mixture of any two or more of the foregoing. Suitable wetting agents include, for example, sodium lauryl sulfate, acacia, benzalkonium chloride, cetomacrogol emulsifying wax, cetostearyl alcohol, cetyl alcohol, cholesterol, diethanolamine, docusate sodium, sodium stearate, emulsifying wax, glyceryl monostearate, hydroxypropyl cellulose, lanolin alcohols, lecithin, mineral oil, onoethanolamine, poloxamer, polyoxyethylene alkyl ethers, polyoxyethylene castor oil derivatives, polyoxyethylene sorbitan fatty acid esters, polyoxyethylene stearates, propylene glycol alginate, sorbitan esters, stearyl alcohol and triethanolamine, or a mixture of any two or more of the foregoing.

In another aspect of the present invention, the sustained-release composition of the present invention comprises a semi-permeable wall surrounding the active compound, the semi-permeable wall being permeable to the passage of fluid but impermeable to the passage of the active compound. The composition includes one or more exits through the semi-permeable wall for sustained release of the active compound, in accordance with the method disclosed in U.S. Pat. No. 5,674,895. In such cases, the active compound can be placed inside the semi-permeable wall alone or as a sustained-release formulation such as with a matrix and/or film-coating.

In another embodiment, an intact film coat with pores for releasing drug through osmotic action can be produced as described in U.S. Pat. No. 5,256,440. According to this approach, a sustained-release drug core is coated with a film that comprises a detachable zone and a fixed zone, wherein the detachable zone, when exposed to an environment of use, detaches from the device to expose a portion of the surface of the compressed core beneath the detachable zone of the film coating, and the fixed zone remains attached to the compressed core. The pores are produced by inscribing (i.e., intagliation) one or more areas on the surface of a drug core prior to coating. An aqueous dispersion of a polymeric coating, i.e., latex, is then applied to the intagliated dosage form core. When placed in an aqueous environment of use, the film coating within the circumscribed region of the dosage form surface is reproducibly detached, leaving a coated core tablet with a predefined discrete portion of the core surface exposed to the environment of use.

In another approach, an intact film coat with pores can be formulated by preparing a film coating where an insoluble polymer such as cellulose acetate is mixed with a soluble material such urea or sucrose. Appel et al., *Pharm. Res.*, 8:600 (1991). After coating, the soluble material becomes detached from the film coat, leaving small pores for releasing drug. Rates of release varying from 1 to 100% can be achieved by varying the coating thickness, pore-former level, and plasticizer type and concentration (id.).

The compression tablet described above also can include multiple layers, each compressed in succession (i.e., a multiple-compression tablet), each layer having a discrete zone, e.g., one for rapid release and one for delayed release, both of which combine to produce sustained release. See U.S. Pat. No. 4,996,061. Such tablets include a fully encased tablet with the outer material completely surrounding the inner material, a layered tablet, which is made up of two or more distinct layers or discrete zones of granulation compressed together with the individual layers lying one on top of another, and the inlay tablet, also referred to as a dot, or bull's-eye tablet, where one surface of the zone corresponding to an inner core zone is exposed (id.).

To obtain the gastroresistance, cellulose, acetophthalate, cellulose acetopropionate, cellulose trimellitate, acrylic and methacrylic polymers and copolymers with different molecular weight and solubility dependent on different pH values may be applied as a polymer coating. See U.S. Pat. No. 5,399,359. The materials may be applied on the finished pharmaceutical form (core+external layer) by the classic film-coating process using solutions in organic solvents or aqueous dispersions and operating by nebulization in basin or in fluidized bed. The gastroresistant and enterosoluble materials may also be used in association with retarding polymers.

A compressed core containing the active compound and a film coating around the core also can comprise a sugar coating containing a further dose of active drug around the seal-coated core as described in U.S. Pat. No. 4,248,858. Sustained-release compositions of the present invention also can comprise multiple compartments as described for capsules in U.S. Pat. No. 5,672,359. In a three compartment design, the outer compartment may incorporate the active compound or an odoriferous agent and excipients into a layer that coats and thus surrounds the intermediate component of the capsule. This outer component represents the rapid or instantaneous release portion of the delivery system. The intermediate compartment comprises a powder formulation that represents the intermediate rate of release portion of the delivery system. The innermost compartment incorporates the active compound in a slow-release formulation as described above or as a multiparticulate form, such as small pellets, which may be coated or uncoated.

Methods of Preparation

A sustained-release composition according to the invention may be formed into a solid dosage presentation according to conventional processes. The pharmacologically active compound and matrix, together with other optional pharmaceutically acceptable excipients, are mixed and then compressed to produce a solid formulation (Example 2). In one such method, the pharmacologically active compound is mixed with a minor proportion of the matrix material of the present invention to form a dry mixture of powders. The mixture is then granulated using a binder material in a solvent such as an alcoholic solvent, e.g., isopropyl alcohol or a mixture of a miscible organic solvent and an aqueous solvent. The wet granular mass is then dried. Other ingredients can then be added to the granules and compressed into tablets. Alternatively, if the nature of the active compound permits, all the ingredients may be dry mixed, including excipients, to form a homogeneous blend, which is then compressed to give a tablet of the correct weight.

The solid formulations according to the invention should be compressed to a sufficient hardness to prevent the premature ingress of the aqueous medium into the core and prevention of surface pitting and breakage during coating of the core. When the final product to be manufactured is tablets, the complete mixture, in an amount sufficient to make a uniform batch of tablets, is subjected to tableting in a conventional production scale tableting machine at an appropriate pressure. Typical compression forces are about 1,000 to about 8,000 pounds.

The application of specialized coatings can be by known methods such as film coating in conventional pans or film coating in a fluidized bed suspension coating apparatus. The conventional pan coating process involves application of the coating as a film using the coating material in a solution or suspension, which is applied to the incipient beads while they are in constant motion. Heat is generally applied to dry the coating.

The fluidized bed coating process involves the application of the coating material in a solution or suspension using a spray nozzle to atomize the coating solution or suspension for application to the incipient beads, which are in motion in the fluidized bed apparatus. Generally, in beads that are to be coated, the incipient beads move up a column where the coating is applied and are dried in an expansion chamber. If tablets are to be coated, the process is the same, except that no column is used. This process is cyclic in nature, occurring repeatedly until the desired amount of coating is applied. For example, see REMINGTON'S PHARMACEUTICAL SCIENCES, supra, and THE THEORY AND PRACTICE OF INDUSTRIAL PHARMACY, Lackman, Liberman and King, eds. (Lea and Febiger, Philadelphia, PA, 1970).

Active Compound Dosage

The sustained-release compositions of the present invention are administered in a "therapeutically effective amount" if the amount administered produces a physiologically significant effect. A physiologically significant effect results in a detectable change in the physiology of a recipient patient. In the present context, for example, a physiologically significant effect for an antispasticity agent results in the alleviation of one or more symptoms of spasticity, while the effect of an anticonvulsant agent is physiologically significant if the presence of the agent results in the reduction of the severity, number, or duration of convulsions. Similarly, for each of the pathologies recited above, the effect of a compound is physiologically significant if, upon administration to a patient, it can alleviate or reduce a clinically recognized symptom of that pathology.

The indicated dosage of isovaleramide and related compounds in treating CNS-effected disorders such as epilepsy or spasticity is on the order of 50 to 2400 mg per dose or 1–40 mg/kg body weight. The precise dose depends upon several factors including the nature and dose of the active compound, the particular sustained-release formulation, and the potential for inter-subject variability.

For use as an anti-convulsant, an effective concentration of isovaleramide in the serum is expected to be about 5 to 15 µg/ml with a target concentration of about 10 µg/ml. Thus, for a 70 kg patient with a plasma clearance of about 150 ml/h for isovaleramide (NPS 1776), a 1200 mg dose of isovaleramide administered twice daily (2400 mg daily dose) should achieve the target therapeutic steady state plasma concentration of about 10 µg/ml. The sustained-release formulations of the present invention provide a steady rate of drug release for at least about 8 hours and more preferably for at least about 12 hours. However, drug release rates exceeding 12 hours also are contemplated.

In addition to use in humans, isovaleramide and related compounds can be used to treat disorders of the CNS (e.g., convulsions, spasticity or anxiety) in animals such as cats, dogs, birds, horses, cattle, mink, poultry, and fish. In such cases the active compound may be administered by injection or other systemic routes, such as transdermal or transmucosal administration (for example, rectal administration via suppositories), or orally, including by addition to food or drink. The indicated oral dosage of isovaleramide and/or related compounds per kilogram of body weight for convulsions or spasticity in non-human animals is about 50–1200 mg/kg, depending upon the species of animal and the route of administration.

3. Exemplary Pathologies Ameliorated by a Modulation of CNS Activity

A description of various CNS-related conditions and their treatment by active compounds used in sustained-release formulations of the present invention including, for example, epilepsy, spasticity, convulsive disorders, affective mood disorders, neuropathic pain syndromes, headaches, restlessness syndrome, movement disorders, have been described in WO 98/08498A1 and U.S. Pat. No. 6,589,994. CNS-related conditions and treatment by the above active compounds also has been described previously for anxiety, sedation and hypnotic activity in U.S. Pat. No. 5,506,268. Additional conditions for application of the sustained-release compositions of the invention include cerebral insult and neuroprotection and substance abuse/craving states as described below.

CEREBRAL INSULT AND NEUROPROTECTION: Excitatory neurotransmitters such as glutamate and aspartate, as well as a variety of voltage-gated ion channels, are thought to play a central role in mediating cell death after a variety of cerebral insults including, but not limited to, ischemia, trauma, seizure and hypoglycemia. Many studies have shown that compounds or therapeutic strategies that decrease excitatory neurotransmission, for example, glutamate antagonists, ion channel blockers, and the like, elicit a neuroprotective effect in animal models of cerebral insults.

Recent studies have shown that compounds such as GABAergic agents (chlormethiazole, valproate or muscimol) that enhance inhibitory neurotransmission, also can elicit a neuroprotective effect following the same type of cerebral insults described above (Lyden, in "Neuroprotective Agents and Cerebral Ischaemia," IRN 40, Academic Press Limited, Chapter 10, (1997)). GABA and glycine are the primary inhibitory neurotransmitters in the mammalian central nervous system and, therefore, it is expected that enhancement of inhibitory neurotransmission via GABA or glycine agonists as well as via other agents that have been shown to increase GABA or glycine inhibitory neurotransmission (GABA/glycine re-uptake inhibitors, GABA/glycine metabolic inhibitors, GABA/glycine synthesis enhancers, GABA/glycine receptor modulators, etc.) also will produce a neuroprotective effect. Studies have shown that the combination of the GABA agonist muscimol and the glutamate antagonist, MK-801 appeared to confer an added neuroprotective effect over either agent alone, although the effect was modest (Lyden, supra, (1997)).

Kindling has been proposed as a model to search for drugs with antiepileptogenic efficacy (Wada, *Epilepsia*, 19:217–227(1974); Sato et al., *Epilepsy Res.*, 5:117–124 (1990); Silver et al., *Ann. Neurol.*, 29:356–363(1991). The term "antiepileptogenic" refers to the idea of inhibiting the processes that underlie the development of epilepsy. "Anticonvulsant," on the other hand, refers to the actual inhibition of seizures in an epileptic model.

Various anticonvulsants that have been shown to delay the acquisition of seizures in animal models of kindling have been proposed to be antiepileptic versus anticonvulsant i.e., the compounds are neuroprotective and block the development of seizures rather than merely blocking the seizure once the disorder is in place (White et al., "Experimental Selection, Quantification, and Evaluation of Antiepileptic Drugs (99–110) in *Antiepileptic Drugs, Fourth Edition*, R. H. Levy, R. H. Matson, and B. S. Meldrum, eds., Raven Press Ltd., Chapter 7, (1995)). Seizure kindling models are characterized by giving a sub-seizure eliciting electrical or chemical stimulus (i.e., sub-threshold) over a period of time (Goddard et al., *Exp. Neurol.*, 25: 295–330, (1969)). The majority of initially non-convulsive animals that are exposed to such stimuli over a number of days, eventually exhibit seizure activity to these stimuli, have a permanently lowered threshold, exhibit altered manifestations of normal behavior and, therefore, are considered "kindled." The kindling-phenomenon has been proposed to underlie the development of disorders such as certain types of epilepsy syndromes. Several kindling models of seizure development have been characterized.

Compounds that have been shown to delay or block acquisitions of seizures in these kindling models have been suggested to be a possible effective therapy following cerebral insults including, but not limited to, ischemia, haemorrhagic stoke, trauma, infection, seizure and hypoglycemia that can lead to an elevated incidence of seizure disorders ("The Epilepsies: Etiologies and Prevention," Kotagal and Luders, Eds., (1999)).

SUBSTANCE ABUSE/CRAVING: Anticonvulsants such as carbamazepine, that have shown efficacy in kindled models of epilepsy, have also demonstrated efficacy in reducing the symptoms of affective mood disorders and substance abuse/craving in patients (Post, et al., *Ann. N.Y. Acad. Sci.*, 537:292–308(1988); Post, et al., *Epilepsia*, 25:234–239(1984); Post, et al., *Psychopharmacol.*, 72:189–196(1981); Halikas et al., Lancet, 8638:623–624 (1989); Blumer et al., *Compr. Psychiatry*, 29(2):108–122 (1988)). Post et al., *Biol. Psychiatry*, 11(4):403–419 (1976), have demonstrated a pharmacologic (chemical) kindling model employing subconvulsive doses of cocaine as the stimulus. The progressive human response to high cocaine usage such as irritability, restlessness, hypervigilance, and paranoia may be a human equivalent of the kindling phenomenon observed in animals.

Several kindling models of seizure development have been characterized. Seizure kindling models are characterized by administration of a sub-seizure eliciting electrical or chemical stimulus (i.e., sub-threshold) over a period of time (Goddard et al., supra, (1969)). The majority of initially non-convulsive animals that are exposed to such stimuli over a number of days eventually exhibit seizure activity to these stimuli, have a permanently lowered threshold, exhibit altered manifestations of normal behavior and therefore are considered "kindled." A kindling phenomenon has been proposed to underlie the development of disorders such as certain types of epilepsy syndromes, substance abuse/craving and affective mood disorders such as bipolar (Post et al., supra, (1981, 1984, and 1988); and Ballenger, et al., *Br. J. Psychiatry*, 133:1–14, (1978).

The pharmaceutical compositions of the invention display anticonvulsant activity and efficacy in animal models of kindling and, accordingly, the inventive pharmaceutical compositions should be useful in treating conditions associated with substance abuse/craving.

4. Demonstrating Therapy-Implicating Activity

The suitability and effectiveness of a given sustained-release pharmaceutical formulation for the alleviation of a pathology, as discussed above, can be demonstrated using animal models such as (but not limited to) those described below.

(a) The Mutant Spastic Mouse

The mutant spastic mouse is a homozygous mouse that carries an autosomal recessive trait of genetic spasticity due to a deficit of glycine receptors throughout the central nervous system. This application of this animal model to spasticity drug testing has been described previously in WO 98/08498A1.

(b) The Acute/Chronic Spinally Transected Rat and the Acute Decerebrate Rat

There are several models of spasticity including the acute decerebrate rat, the acute or chronic spinally transected rat, and the chronically spinal cord-lesioned rat. Wright, J., et al., *Clin. Orthop.*, 253:12 (1990). These models have also provided methods to test various treatment paradigms that have led to similar treatments being tested in humans and are described in greater detail in WO 98/08498A 1.

(c) Primary Observation Irwin Test in the Rat

This method is based on that described by Irwin, *Psychopharmacologia* 13: 222–57 (1968). It is used to detect physiological, behavioral, and toxic effects of a test substance, and indicates a range of dosages that can be used for later experiments. This method is described in greater detail in WO 98/08498A1.

(d) Rotarod Test in the Rat and Mouse

This is a test of neurological deficits using the method described by Dunham et al., *J. Am. Pharm. Assoc.*, 46: 208–209 (1957), involving placement of rats or mice on rotating rod. This model is described in greater detail in WO 98/08498A 1.

(e) Anticonvulsant Activity

There are numerous in vivo models involving different kinds of seizures and behavioral effects that are relevant for clinically distinct forms of epilepsy. These include, for example, the Frings audiogenic seizure-susceptible mouse for reflex epilepsy, which has been described in greater detail in WO 98/08498A 1.

(f) Anti-Manic Activity

The amphetamine-induced hyperactivity model in rats can be used to assess the possible use of compounds in the treatment of affective mood disorders. In addition to being a test for classical and atypical antipsychotic activity, this procedure has also been proposed as a simple animal model of manic behavior. Costall et al., *Brain Res.*, 123: 89–111 (1977).

(g) Neurogenic Inflammation of The Meninges

Neurogenic inflammation within the meninges has been proposed as an event in the underlying pathology of migraine headaches. Lee et al., *Brit. J. Pharmacol.*, 116: 1661–1667 (1995). Compounds are tested for their ability to block the leakage of radiolabeled bovine serum albumin within the dura mater post trigeminal stimulation.

(h) Analgesic Properties

There are many whole-animal assays for determining analgesic properties, such as writhing, hotplate, tail flick, arthritic pain, paw pressure tests, and the Bennet or Chung models of neuropathic pain. Albe-Fessard et al., in ADVANCES IN PAIN RESEARCH AND THERAPY, Chapter 13, pages 11–27, (Raven Press, 1990).

(i) Movement Disorders and Restlessness Syndromes

Animal models exist for the study of movement disorders and restlessness syndromes, for example, drug-induced akathisias, serotonin syndrome, rotation induced by unilateral nigral lesions (Lloyd et al., *Med. Biol.*, 65(2–3):159–65 (1987)). Additionally, individual case reports of anecdotal efficacy of compounds in humans have been a source for support for these indications. Mellick et al., *Am. J. Emerg. Med.*, 13(1):96 (1995); and Olson et al., *Am. J. Med.*, 102:60–66 (1997).

(j) Neuroprotection

Kindling has been proposed as a model that can be used to identify drugs with antiepileptogenic efficacy (Wada, supra (1974); Sato et al., supra (1990); and Silver et al., supra (1991). The term "antiepileptogenic" refers to the idea of inhibiting the processes that underlie the development of epilepsy thereby providing a "neuroprotective" effect. "Anticonvulsant," on the other hand, refers to the actual inhibition of seizures in an epileptic model. Several models of kindling are useful. The amygdala-kindled rat is such a model (Tober, *Eur. J. Pharmacol.*, 15:163–169(1996)). Seizure kindling models are characterized by giving a sub-seizure eliciting electrical or chemical stimulus (i.e., sub-threshold) over a period of time (Goddard et al., supra (1969)). The majority of initially non-convulsive animals that are exposed to such stimuli over a number of days, eventually exhibit seizure activity to these stimuli, have a permanently lowered threshold, exhibit altered manifestations of normal behavior and therefore are considered "kindled."

Acute cerebral insults such as status epilepticus, traumatic injury and stroke induce damage to selective neuronal populations in the hippocampus (Matsuyama et al., *J. Cereb. Blood Flow Metab.*, 13:229–234(1993); and Sloviter, *Science*, 235:73–76(1987)), suggesting that substances designed to prevent the neuronal damage that occurs in a variety of human neurological diseases would be therapeutically useful. In Jolkkonen et al., *Neuroreport*, 7:2031–2035 (1996), it was found that augmentation of GABAergic inhibition by chronic infusion of the GABA transaminase inhibitor, vigabatrin, prevented the delayed seizure-induced damage following kainate-induced status epilepticus.

Stroke in humans is a highly variable clinical condition, dependent upon pre-existing disease in a patient, the site and severity of the stroke, the type of stroke (ischemic or hemorrhagic), and the time from onset to presentation for treatment. A number of animal models of stroke have been developed over the past several years to aid in our understanding of the pathophysiological mechanisms of neuronal injury and to allow for the evaluation of potential neuroprotective agents (Ginsberg et al., *Stroke*, 20: 1627–1642 (1989); and Hunter et al., *Trends. Pharmacol. Sci.* 16:123–128 (1996)). A major goal of these animal models has been to reduce the biological variability, by controlling or eliminating the variables mentioned above, to facilitate data analysis and interpretation. In doing so, however, these animal models do not perfectly mimic the human condition.

(k) Substance Abuse/Craving

Kindling phenomenon has been proposed to underlie the development of disorders, such as epilepsy, substance abuse/craving, and affective mood disorders, such as bipolar (Post et al. 1981; Post et al., 1984; Ballenger et al., 1978; Post et al., 1988). Anticonvulsants, such as carbamazepine, that have shown efficacy in kindled models of epilepsy, have also demonstrated efficacy in reducing the symptoms of affective mood disorders and substance abuse/craving in patients (Post and Weiss, supra (1989); Halikas et al., supra (1989); and Blumer et al., supra (1988)). Post et al., *Biol. Psychiatry* 11:403–419(1976), have demonstrated a pharmacologic (chemical) kindling model employing subconvulsive doses of cocaine as the stimulus. The progressive human response to high cocaine usage such as irritability, restlessness, hypervigilance, and paranoia may be a human equivalent of the kindling phenomenon observed in animals. Recently, the anticonvulsant drug, vigabatrin, was proposed as a possible treatment for cocaine or nicotine craving (Dewey, et al., *Synapse*, 31:76(1999)).

The therapeutic effects of isovaleramide, isovaleric acid, and related compounds, as illustrated in various of the assays described above, are exploited to unexpected advantage in sustained-release formulations of the present invention. These formulations can be used to treat the pathologies described above, including, for example, spasticity, bipolar affective disorder and convulsions/seizures. With this background, the present invention will be understood more readily by reference to the following examples, which are provided for purposes of illustration and are not intended to be limiting of the invention.

EXAMPLE 1

Pharmacokinetic Properties of Isovaleramide Orally Administered in Humans

Isovaleramide (NPS 1776) was orally administered in a double-blind, placebo-controlled, ascending single dose study conducted in two groups of healthy young male Caucasian subjects and one group of healthy young female Caucasian subjects to investigate the safety, tolerability, pharmacodynamics and pharmacokinetics of the drug. Various amounts of the drug were dissolved in 250 mL of a flavored soft drink (powdered soft drink diluted in mineral water) and administered as an oral solution.

Safety and Tolerability:

Isovaleramide was well tolerated following oral administration of 100 to 1600 mg to healthy male subjects. There were few drug-related adverse events during the study, and all were mild in severity. The most common adverse events were polyuria and headache. There were no dose-related trends in the incidence or severity of adverse events, or any difference in the incidence or severity of adverse events reported. Similar results were obtained in a 1200 mg dose level female group administered the drug for gender comparison. For all dose levels, there were no clinically significant drug-or dose-related changes in vital signs (body temperature, supine and standing blood pressure and heart rate), 12-lead ECG, clinical laboratory assessments or physical examination.

Pharmacokinetics:

Isovaleramide administered orally in the absence of a sustained-release formulation was rapidly absorbed and rapidly eliminated in human subjects (Table 1). Systemic exposure to the drug increased with increasing oral doses from 100 to 1600 mg in male subjects. The increase in $C_{max}$ and AUC was slightly greater than proportional to the increase in the dose level. Values for $t_{max}$ and t½ did not markedly vary with the dose, while the plasma clearance and volume of distribution decreased with increasing dose. Pharmacokinetic parameters of NPS 1776 (1200 mg dose) in females were not markedly different to those in males with the exception of t½, which was slightly lower in females (1.89 h) than in males (2.43 h).

TABLE 1

Pharmacokinetic Parameters for Oral Isovaleramide in Male Humans

| Parameter | Dose of isovaleramide | | | | | |
|---|---|---|---|---|---|---|
| | 100 mg | 200 mg | 400 mg | 800 mg | 1200 mg | 1600 mg |
| $C_{max}$* ($\mu$g/mL) | 1.51 (1.30–1.76) | 3.32 (2.82–3.89) | 6.84 (6.37–7.34) | 16.4 (13.7–19.5) | 27.9 (23.3–33.1) | 39.3 (36.8–42.1) |
| t1/2‡ (h) | 2.70 (2.16–3.22) | 2.61 (1.93–3.25) | 2.50 (2.08–2.92) | 2.35 (2.13–2.96) | 2.43 (1.92–2.80) | 2.65 (2.12–3.36) |
| CL/F§ (mL/h) | 230 (37.7) | 185 (18.8) | 188 (29.8) | 164 (23.7) | 148 (26.8) | 130 (17.5) |

*Geometric mean (95% confidence intervals)
§Arithmetic mean (SD)
‡Harmonic mean (min-max)

The results show that isovaleramide has a short half-life of about 2.5 hours in humans when orally administered in the absence of a sustained-release formulation. For all doses, the maximum drug concentration was achieved in less than one hour and typically in about 30 minutes following administration.

For a 2.5-hour half-life, a single dose of drug results in about a 10-fold change in the drug concentration in the blood over a 12-hour period. If one assumes an effective target blood concentration of the drug of about 10 $\mu$g/mL, then administration of a 1200 mg dose of the drug falls below the effective concentration at about 5 hours after administration. That is, 1200 mg results in an initial maximum blood concentration of about 27 mg ($C_{max}$), which decreases four fold—two half lives—to about 6–7 mg at five hours after injection.

Thus, use of a sustained-release formulation could avoid having to administer, say, a 1200 mg dose every 4 to 6 hours, in order to maintain a therapeutic concentration of drug in the serum.

EXAMPLE 2

Preparation of Sustained-Release Pharmaceutical Formulation of Isovaleramide

EXAMPLE 2.1

This example describes the preparation of film coated tablets of isovaleramide (NPS 1776) which were designed to release drug in a sustained manner. The formulations were designed to deliver a specific amount of drug over a specific course of time to achieve a specific plasma drug concentration, while minimizing peak to trough differences that occur in vivo. This was achieved despite the fact that the tablet contains a very high drug load and the drug is very water soluble.

Sustained release was achieved with two barriers. An outside barrier is an ethyl cellulose/hydroxypropyl methyl cellulose film coat that retards diffusion of water into the tablet core and acts as a barrier against drug diffusion out from the inner core of the tablet. An inside barrier comprises xanthan gum in the tablet core matrix, which hydrates and swells to form a viscous gel.

A. Manufacturing Procedure for Dual Barrier Tablet

Preparation of the Tablet Core

1. Active drug (e.g., Isovaleramide; NPS 1776; Oread, Lawrence, Kans.; cGMP grade) was dispersed by passage through a #30 mesh screen.

2. Drug, xanthan gum (e.g., XANTURAL®; Monsanto, St. Louis, MO; NF grade) and lactose (e.g. monohydrate form, spray dried,: Oread, Palo Alto, Calif.; NF grade) were mixed into a 1-L glass jar and blended in a Turbula mixer for four minutes at 96 rpm.

3. Magnesium stearate (e.g. Oread, Palo Alto, Calif.; NF grade) was added and the mixture blended for one minute.

4. The final blend was compressed into caplets using 0.32-inch×0.75-inch×0.060-inch tooling to a target weight of 800 mg and a target hardness of 8 kP, and target thickness of 0.25 inch.

Coating of the Tablet Cores

1. Hydroxypropyl methylcellulose (HPMC; e.g., Dow Chemical Co., Midland, MI; NF grade) solution was prepared by adding HPMC slowly to purified water heated to approximately 80° C. The solution was allowed to cool to room temperature by placing vessel in a cold water bath. Additional water was added to prepare the final requisite amount of HPMC solution.

2. AQUACOAT® ECD/dibutyl sebecate mixture was prepared by adding dibutyl sebacate (DBS: e.g., Morflex Inc., Greenboro, N.C.; NF grade) to AQUACOAT® ECD (e.g., FMC Pharmaceutical Division, Philadelphia, Pa.) while mixing. Mixing was continued for a minimum of 30 minutes.

3. The HPMC solution was added slowly to the AQUACOAT® ECD/DBS mixture.

4. The core tablets were loaded into a coating apparatus (Vector LCDS 3 coater) fitted with a 1.3 liter coating pan and warmed until an outlet temperature of 40° C. was reached.

5. The tablets were spray coated until the planned theoretical weight gain (based on core tablet weight) was achieved, however, after curing, the actual coating solids applied were less than the theoretical value (e.g., 8% or 15% theoretical can be 5% and 12% coat, respectively after curing). Thus, extra spray may need to be added to account for the loss upon curing. Conditions for coating were as follows:

| | |
|---|---|
| Inlet temperature | 70° C. |
| Outlet temperature | 40–43° C. |
| Spray rate | 4–5 g/min |
| Pan speed | 14 rpm |
| Fluidizing air | 30–40 scfm |
| Atomization air pressure | 26 psi |

6. Spraying was stopped when the requisite amount of coating suspension was applied. The tablets were dried for approximately 5 minutes in the coating pan. The inlet temperature was adjusted during drying to keep outlet temperature below 45° C.

7. The tablets were cured in an oven at 60° C. for 18 hours.

B. Composition Analysis of Sustained-Release Tablets

The composition of a variety of sustained release tablets are provided in tables 7–9 below.

TABLE 7

Formulation Composition for a 5% Film-Coated Tablet Containing 400 Mg Isovaleramide (NPS 1776)

| Component | Tablet (mg) | Batch (g) | Percent (% w/w) |
|---|---|---|---|
| Isovaleramide (NPS 1776) | 400.0 | 200.0 | 47.6 |
| Xanthan Gum | 56.0 | 28.0 | 6.7 |
| Lactose Monohydrate, Spray-dried | 340.0 | 170.0 | 40.5 |
| Magnesium Stearate | 4.0 | 2.0 | 0.5 |
| Core Tablet Total Weight | 800.0 | 400.0 | 95.3 |
| AQUACOAT ® ECD (solids wt.) | 24.4[1] | 24.4[2] | 2.9 |
| Hydroxypropyl methylcellulose | 9.8 | 9.8 | 1.1 |
| Dibutyl sebacate | 5.8 | 5.8 | 0.7 |
| Purified water[3] | (63.1) | (63.1) | N/A |
| Coated Tablet Total Weight | 840.0 | 840.0 | 100.0 |

N/A = Not Applicable,
[1]Solids content provided by 81.3 mg of suspension,
[2]Solids content provided by 81.3 g of suspension,
[3]Removed during processing.

TABLE 8

Formulation Composition for a 12% Film-Coated Tablet Containing 400 Mg Isovaleramide (NPS 1776)

| Component | Tablet (mg) | Batch (g) | Percent (% w/w) |
|---|---|---|---|
| Isovaleramide (NPS 1776) | 400.0 | 200.0 | 44.6 |
| Xanthan Gum | 56.0 | 28.0 | 6.3 |
| Lactose Monohydrate, Spray-dried | 340.0 | 170.0 | 37.9 |
| Magnesium Stearate | 4.0 | 2.0 | 0.4 |
| Core Tablet Total Weight | 800.0 | 800.0 | 89.2 |
| AQUACOAT ® ECD (solids wt.) | 58.8[1] | 58.5[2] | 6.5 |
| Hydroxypropyl methylcellulose | 23.4 | 23.4 | 2.6 |
| Dibutyl sebacate | 14.1 | 14.1 | 1.6 |
| Purified water[3] | (151.4) | (151.4) | N/A |
| Coated Tablet Total Weight | 896.0 | 896.0 | 100.0% |

N/A = Not Applicable,
[1]Solids content provided by 195.1 mg of suspension,
[2]Solids content provided by 195.1 g of suspension,
[3]Removed during processing.

TABLE 9

Formulation II: Composition of a 9% Film-Coated Tablet Containing 400 Mg Isovaleramide

| Component | Tablet (mg) | Batch (g) | Percent % w/w |
|---|---|---|---|
| Isovaleramide (NPS 1776) | 400.0 | 400.0 | 45.5 |
| Xanthan Gum | 56.0 | 56.0 | 6.4 |
| Lactose Monohydrate, Spray-dried | 340.0 | 340.0 | 38.6 |
| Magnesium Stearate | 4.0 | 4.0 | 0.5 |
| Core Tablet Total Weight | 800.0 mg | 800.0 mg | 91.0 |
| AQUACOAT ® ECD (solids wt.) | 48.8[1] | 48.8[2] | 5.5 |

TABLE 9-continued

Formulation II: Composition of a 9% Film-Coated Tablet Containing 400 Mg Isovaleramide

| Component | Tablet (mg) | Batch (g) | Percent % w/w |
|---|---|---|---|
| Hydroxypropyl methylcellulose | 19.5 | 19.5 | 2.2 |
| Dibutyl sebacate | 11.7 | 11.7 | 1.3 |
| Purified water[3] | (126.2) | (126.2) | N/A |
| Coated Tablet Total Weight | 880.0 mg | 880.0 g | 100.0% |

N/A = Not Applicable,
[1]Solids content provided by 162.6 mg of suspension,
[2]Solids content provided by 162.6 g of suspension,
[3]Removed during processing.

TABLE 10

Formulation III: Composition of a 12% Film-Coated Tablet Containing 600 Mg Isovaleramide

| Component | Tablet (mg) | Percent (% w/w) |
|---|---|---|
| Isovaleramide (NPS 1776) | 600.0 | 66.0 |
| Xanthan Gum | 56.0 | 6.2 |
| Lactose Monohydrate, Spray-dried | 140.0 | 15.4 |
| Magnesium Stearate | 4.0 | 0.4 |
| Core Tablet Total Weight | 800.0 | 88.0 |
| AQUACOAT ® ECD (solids wt.) | 48.7[1] | 5.4 |
| Hydroxypropyl methylcellulose | 48.7 | 5.4 |
| Dibutyl sebacate | 11.7 | 1.2 |
| Purified Water[2] USP | (213.6) | N/A |
| Coated Tablet Total Weight | 909.1 mg | 100.0% |

N/A Not Applicable,
[1]Solids content provided by 162.4 mg of suspension,
[2]Removed during processing.

EXAMPLE 2.2

This example describes the preparation of multiparticulate compositions of isovaleramide (NPS 1776) which were designed to release drug in a sustained manner. These formulations were designed to deliver a specific amount of drug over a specific course of time to achieve a specific plasma drug concentration, while minimizing peak to trough differences that occur in vivo.

C. Manufacturing Procedure for Multiparticulate Compositions (MPC)

Preparation of the Tablet Core

1. Isovaleramide (NPS 1776) (200–300 gm) was mixed with microcrystalline cellulose (AVICEL PH 101®) and pregelatinized cornstarch (STARCH 1500®) in a small high shear mixer. Water was added such that small agglomerates were formed.

2. The material was extruded through 1.7-mm holes with a small extruder. The extrudate was spheronized with a maurumerizer (available from Luwa, Charlotte, NC) with a plate speed of 1,000 rpm. Beads were formed within 2 minutes and were tray dried in a 50° C. oven overnight.

3. One 700-gm batch of beads (approximately 60% drug loading) was prepared and coated. Materials were screened though an #8 mesh screen to break up large lumps and added to a KG5® high shear mixer (available from Key International, Englishtown, N.J.). The materials were mixed for 2 minutes with an impeller speed of 200 rpm and chopper speed of 2,000 rpm. Water was added at approximately 25 mL/minute and impeller speed was gradually increased to 350 rpm. A total of 375 mL of water was added over 20 minutes. The energy input increased from 36 watts to 460 watts. The material was extruded and spheronized as above.

Coating of the Tablet Cores

4. The beads were coated in a UNIGLATT® coater (available from Glatt Air Technologies, Ramsey, N.J.) with a cellulose acetate butyrate solution. Dissolution of multiparticulate compositions were performed using USP Apparatus 1 (rotating basket) instead of USP Apparatus 2. Conditions for coating were as follows:

| | |
|---|---|
| Inlet air temperature | 48–52° C. |
| Outlet air temperature | 42–44° C. |
| Spray rate | 10 g/min |
| Atomization air pressure | 15 psi |

TABLE 11

700 gram Batch Preparation for Multiparticulate Compositions (MPC) Containing 420 gram Isovaleramide (NPS 1776) and Batch Preparation for Film Coating Solution

| | Batch (g) |
|---|---|
| MPC Components | |
| Isovaleramide (NPS 1776) | 420 |
| AVICEL PH 101 | 224 |
| STARCH 1500 | 56 |
| MPC Total Weight | 700 |
| Coating Solution Components | |
| Cellulose Acetate Butyrate | 63.0 |
| Triethyl Citrate | 18.9 |
| Sucrose | 22.0 |
| Acetone[1] | (1750 mL) |
| Ethanol[1] | (350 mL) |
| Water[1] | (350 mL) |
| Film Coat Total Weight | 103.9 |

[1] Removed during processing.

TABLE 12

Film Coated Multiparticulate Composition (MPC) Formulations Containing Isovaleramide (NPS 1776)

| Component | 1% Film Coat (% w/w) | 4% Film Coat (% w/w) | 6% Film Coat (% w/w) | 8% Film Coat (% w/w) |
|---|---|---|---|---|
| Isovaleramide (NPS 1776) | 59.4 | 57.6 | 56.4 | 55.2 |
| AVICEL PH 101 | 31.7 | 30.7 | 30 | 29.4 |
| STARCH 1500 | 7.9 | 7.7 | 7.6 | 7.4 |
| MPG Percent Total | 99 | 96 | 94 | 92 |
| Cellulose Acetate Butyrate | 0.61 | 2.44 | 3.66 | 4.88 |
| Triethyl Citrate | 0.18 | 0.72 | 1.08 | 1.44 |
| Sucrose | 0.21 | 0.84 | 1.26 | 1.68 |
| Acetone[1] | N/A | N/A | N/A | N/A |
| Ethanol[1] | N/A | N/A | N/A | N/A |
| Water[1] | N/A | N/A | N/A | N/A |
| Coated MPG Total Wt. | 707.1 | 729.2 | 744.7 | 760.9 |
| Coated MPG Total % | 100.0 | 100.0 | 100.0 | 100.0 |

EXAMPLE 3

In Vitro Release and In Vivo Pharmacokinetic Analysis of Sustained-Release Pharmaceutical Formulation of Isovaleramide

EXAMPLE 3.1

Formulation I, Formulation II and Formulation III

This example describes methods to evaluate the efficacy of sustained-release formulations of isovaleramide (Formulation I, Formulation II, and Formulation III) and related compounds. Sustained-release formulations were tested in a standard, 24-hour dissolution assay essentially as described in UNITED STATES PHARMACOPEIA (USP), edition XXIV (Apparatus 2; United States Pharmacopeia, 24, U.S. Pharmacopeial Convention, Inc., Rockville, Md., pages 1941–1947 (2000)). Dissolution of drug was determined in simulated gastric fluid (SGF) without enzymes or in simulated intestinal fluid (SIF) without enzymes as described previously (id., pages 2235–2236). A two-stage media dissolution model, involving two-hour incubation in SGF followed by 22-hour incubation in SIF (id. at 1947: entitled "Delayed-release (Enteric Coated) Article—General Drug Release Standard"), was used to project in vivo drug dissolution and to determine if a formulation has delayed release properties. The amount of drug released into SGF or SIF was determined by C18 reverse-phase high pressure liquid chromatography.

Sustained-release Formulation I was produced as a tablet with a single barrier to retard drug release. Formulation I is the "core" tablet portion of Formulation II, shown in Table 9. Thus, Formulation I contains 400 mg of isovaleramide, xanthan gum and lactose. Oral administration of Formulation I to humans resulted in a peak serum drug concentration of about 4 hours, which is about four times that with isovaleramide itself (Example 1).

Figure 3:
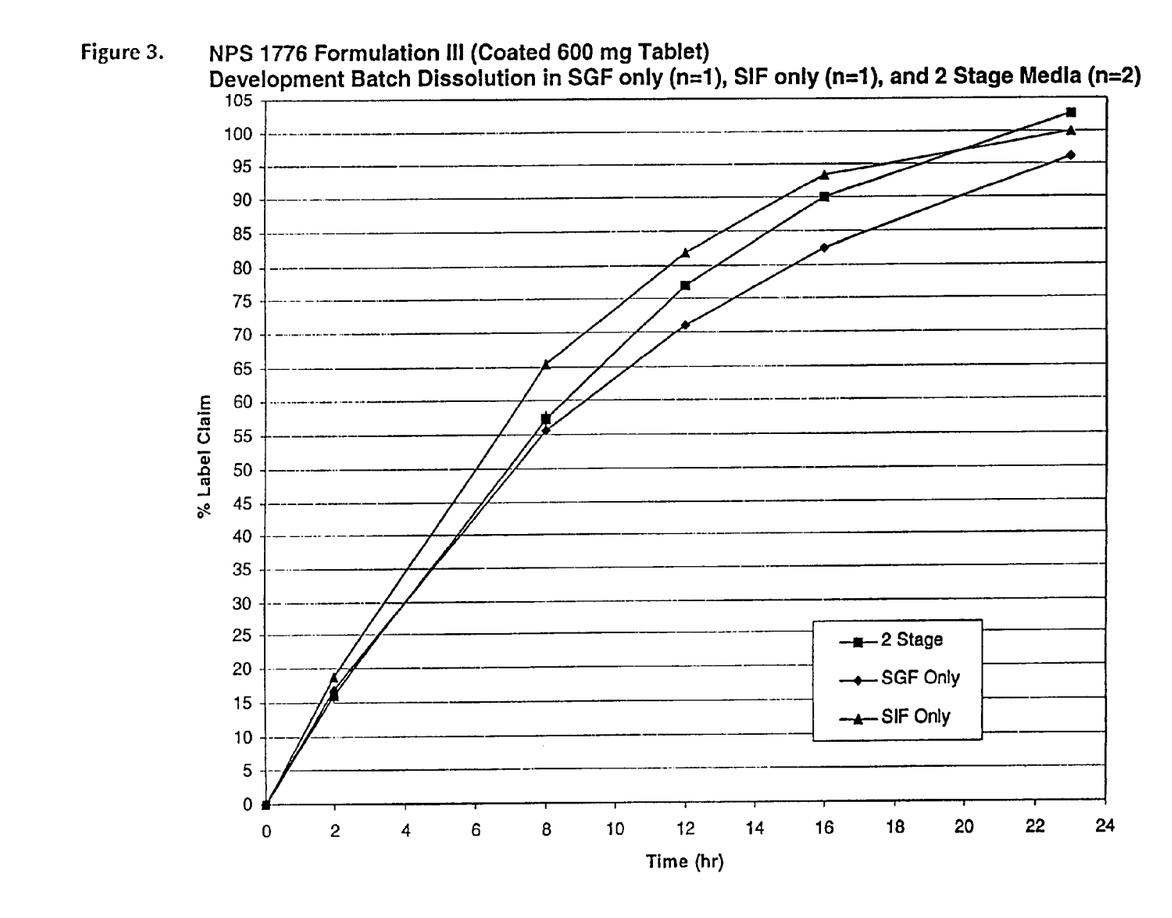
FIG. 3 portrays a 24-hour dissolution profile of film-coated sustained-release tablets containing 600 mg of isovaleramide (Formulation III, Example 2.1). The dissolution assay and subsequent analysis is performed as described in Example 3.1. At 16 hours, over 80% of the drug is released under the two stage media analysis. Drug release rate is similar for SIF and SGF as shown by the individual dissolution profiles.

Sustained-release Formulation II, containing 400 mg isovaleramide, was produced as a tablet with two barriers, to retard drug release as described in Example 2.1, Table 9. In the in vitro drug dissolution assays, Formulation II showed significant delay in dissolution, with greater than 75% of the drug released into the medium after 16 hours in the two stage assay (FIG. 3.1).

Pharmacokinetic analysis of Formulation I and II were performed in two groups of eight human volunteers administered orally either one sustained-release tablet (400 mg dose) or two tablets (800 mg dose). All 800 mg doses and 6/8 of the 400 mg doses of Formulation II had peak serum concentrations occurring between 8–12 hours post administration. This compares with a mean peak concentration occurring at about 3 hours for Formulation I. Formulation II was about 85% orally bioavailable, while Formulation I was about 100% bioavailable.

These results indicated that administering 1200 mg of isovaleramide twice daily (2400 mg daily dose) as Formulation II, with dosing at 12-hour intervals, achieves a target therapeutic steady-state plasma drug concentration of 10 µg/ml. Inter-subject variability was higher than for individuals taking Formulation I. Also, the dissolution rate of Formulation II in the in vitro assay was greater in SIF than SGF, indicating that dissolution probably is pH-dependent for Formulation II. The variability observed in vivo may result from variation in gastric residence times between individuals.

Formulation III differs from Formulation II in that the former has a decreased ratio of AQUACOAT® ECD to hydroxypropyl methylcellulose in the coat. In the two-stage dissolution in vitro assay, over 80% of the drug in Formulation III is released at 16 hours, with little apparent pH-dependency (FIG. 3.1: compare SGF with SIF). These results indicate that a therapeutic steady-state plasma concentration of about 5 to 15 µg/ml (target of about 10 µg/ml) should be achieved in humans who receive two units of Formulation III (i.e., a 1200 mg dose of isovaleramide) at about 12-hour intervals (2400 mg daily dose). The reduction in pH dependency suggests that Formulation III has improved inter-subject variability, relative to Formulation II.

EXAMPLE 3.2

Film Coated MPC Formulations: 1%, 4%, 6%, and 8% MPC Formulations

This example describes methods to evaluate the efficacy of the sustained-release, film coated multiparticulate composition formulations (1%, 4%, 6%, and 8% Film Coated MPCs) of isovaleramide and related compounds. Sustained-release, film coated multiparticulate composition formulations were tested in a standard, 24-hour dissolution assay essentially as described in UNITED STATES PHARMACOPEIA (USP), edition XXIV (Apparatus 1; United States Pharmacopeia, 24, U.S. Pharmacopeial Convention, Inc., Rockville, Md., pages 1941–1947 (2000)). Dissolution of drug was determined in simulated gastric fluid without enzymes (SGF) or in simulated intestinal fluid without enzymes (SIF) as described previously (id., pages 2053, 4082 and 4680). The amount of drug released into SGF or SIF was determined by C18 reverse-phase high pressure liquid chromatography.

Figure 4:
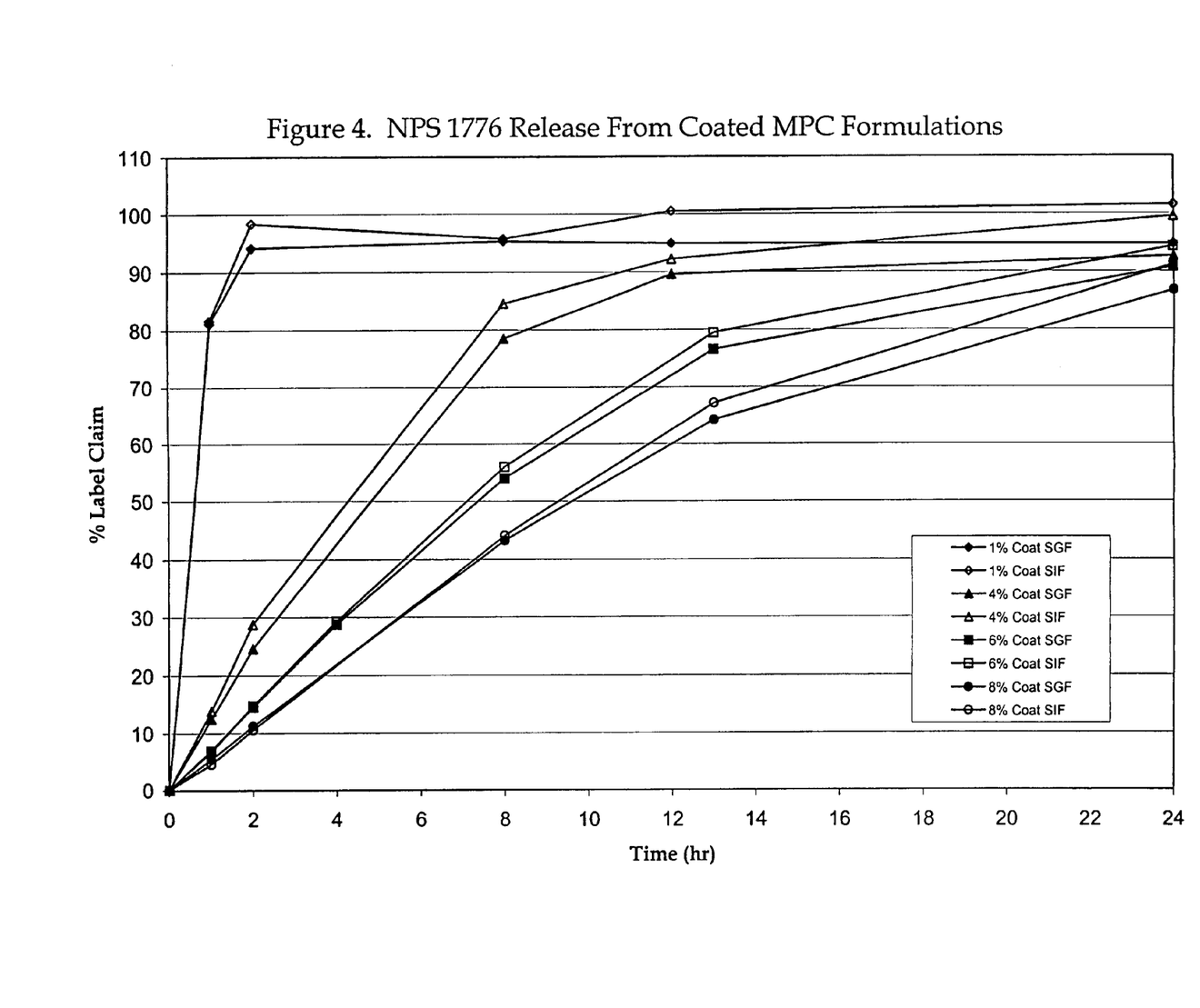
FIG. 4 portrays a 24-hour dissolution profile of film-coated multiparticulate composition formulations containing isovaleramide (Example 2.2). The dissolution assay and subsequent analysis is performed as described in Example 3.2.
Figure 5:
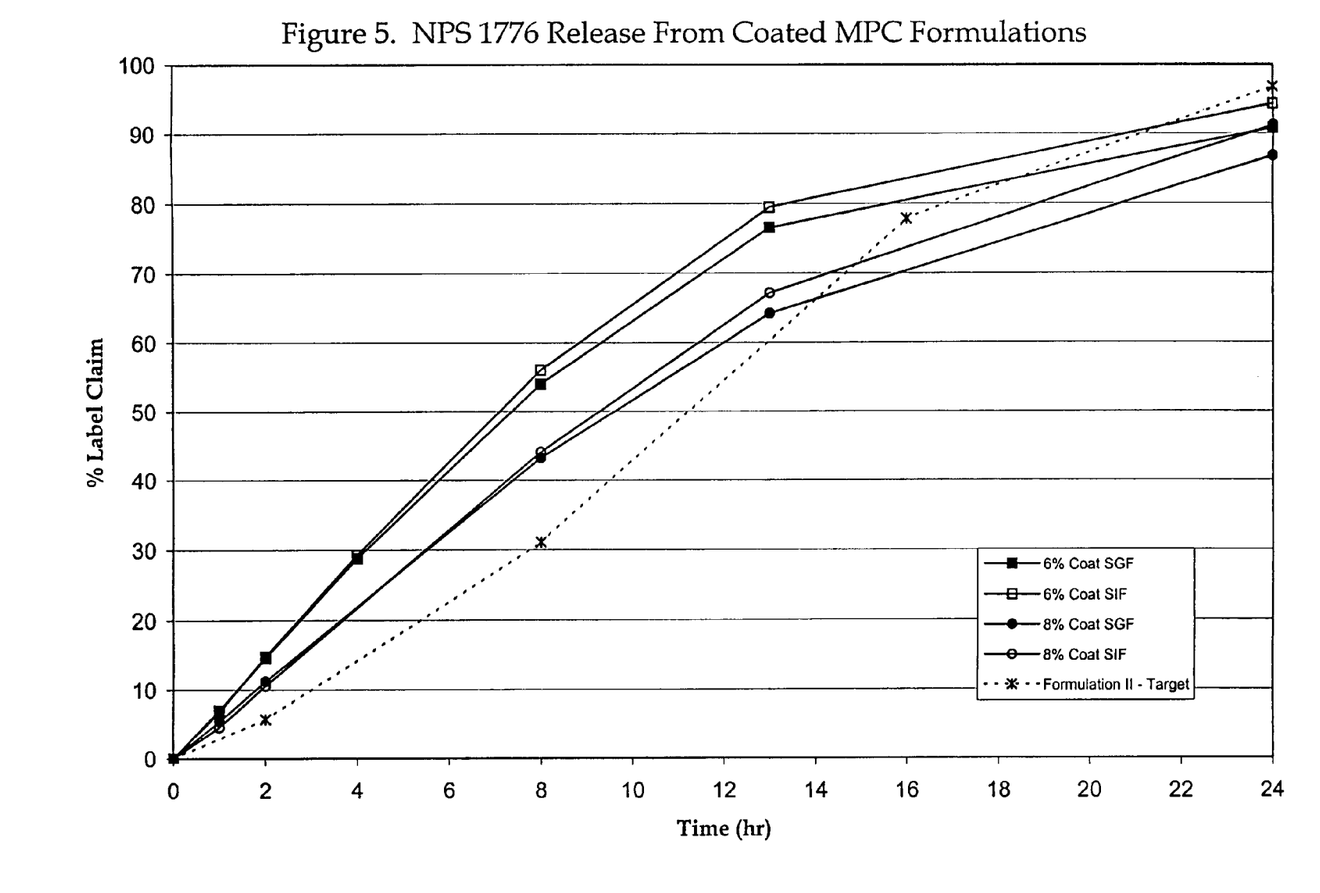
FIG. 5 portrays a 24-hour dissolution profile of the 6% and 8% film-coated multiparticulate composition formulations containing isovaleramide. At 16 hours, approximately 80% of the drug is released. Drug release rate is similar for SIF and SGF as shown by the individual dissolution profiles.

The 1%, 4%, 6%, and 8% Film Coated MPCs demonstrated little difference in drug release in SGF or SIF (FIG. 4). The isovaleramide release profile of the 6%, and 8% Film Coated MPCs were similar to the Formulation II release profile of 80% isovaleramide released in 16 hours (FIG. 5).

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the claims below.

What is claimed is:

1. An oral sustained-release pharmaceutical composition comprising a core matrix comprising a therapeutically effective amount of an active compound, a gelling agent, and a polymeric film coating material comprising a mixture of ethyl cellulose and hydroxypropyl methylcellulose that retards access of liquids to the active compound and/or retards release of the active compound through the film-coating, wherein the amount of the active compound represents from about 40% to about 70% by weight of the oral-sustained release pharmaceutical composition, and wherein the active compound is selected from the group consisting of: isovaleric acid, a pharmaceutically acceptable salt of isovaleric acid, a pharmaceutically acceptable ester of isovaleric acid, a compound having the structure:

wherein
A=H, $CH_3$, or OH,
B=H, OH, or $CH_3$,
X=$CH_2$, $CHCH_3$, $C(CH_3)_2$, —O—, CH(OH), or —$CH_2O$—, Y = —CO—, or —$SO_2$—, and Z = H, $CH_2CO_2H$, or $CH_2CONH_2$, and a compound selected from the group consisting of isovaleramide, 2-methylisovaleramide, 3-methylisovaleramide, 2,2-dimethylisovaleramide, 2,3-dimethylisovaleramide, 2,4-dimethylisovaleramide, 3,4-dimethylisovaleramide, 2,2,4-trimethylisovaleramide, 3-hydroxyisovaleramide, 4-hydroxyisovaleramide, 4-hydroxy-3-methyl-isovaleramide, 2-hydroxyisovaleramide, N-(2-acetamido)isovaleramide, 2-methyl-1-propylsulfonamide, 1-methylethyl sulfamate, 2-methyl-1-propyl sulfamate, isopropyl carbamate, and isobutylcarbamate.

2. The oral sustained-release pharmaceutical composition according to claim 1, wherein the oral sustained-release pharmaceutical composition releases the active compound at a rate sufficient to maintain a therapeutically effective serum concentration of the active compound for at least 8 hours.

3. The oral sustained-release pharmaceutical composition according to claim 1, wherein the oral sustained-release pharmaceutical composition releases the active compound at a rate sufficient to maintain a therapeutically effective serum concentration of the active compound for at least 12 hours.

4. The oral sustained-release pharmaceutical composition according to claim 1, wherein the gelling agent comprises xanthan gum.

5. The oral sustained-release pharmaceutical composition according to claim 1, further comprising at least one excipient.

6. The oral sustained-release pharmaceutical composition according to claim 1, wherein the active compound is isovaleramide.

7. The oral sustained-release pharmaceutical composition according to claim 1, wherein the polymeric coating material further comprises a plasticizer.

8. The oral sustained-release pharmaceutical composition according to claim 1, wherein the oral sustained-release pharmaceutical composition is in the form of a tablet, capsule, or multiparticulate composition.

* * * * *